United States Patent [19]
Levine et al.

[11] Patent Number: 5,676,910
[45] Date of Patent: Oct. 14, 1997

[54] AUTOMATIC BLOOD FILM PREPARATION DEVICE

[75] Inventors: Marshall S. Levine; Daniel S. Levine; David E. Levine, all of Wayne, Pa.

[73] Assignee: Alpha Scientific Corporation, Malvern, Pa.

[21] Appl. No.: 477,980

[22] Filed: Jun. 7, 1995

[51] Int. Cl.$^6$ .................................................. G01N 21/00
[52] U.S. Cl. ........................... 422/65; 422/67; 422/100; 118/100
[58] Field of Search ........................ 118/120, 100, 118/500, 415, 2, 4, 7, 9; 422/65, 66, 67, 100, 104; 436/46

[56] References Cited

U.S. PATENT DOCUMENTS

| | | | |
|---|---|---|---|
| 3,470,847 | 10/1969 | Chapin et al. | 118/100 |
| 3,683,850 | 8/1972 | Grabhorn | 118/100 |
| 3,880,111 | 4/1975 | Levine et al. | 118/4 |
| 4,034,700 | 7/1977 | Bassett et al. | 118/2 |
| 4,061,108 | 12/1977 | Levine et al. | 118/100 |
| 4,096,824 | 6/1978 | Levine et al. | 118/100 |
| 4,151,915 | 5/1979 | Levine et al. | 206/456 |
| 4,319,542 | 3/1982 | Ojima et al. | 118/100 |
| 4,407,843 | 10/1983 | Sasaki et al. | 427/2 |
| 4,516,522 | 5/1985 | Drury et al. | 118/120 |
| 4,828,716 | 5/1989 | McEwen et al. | 210/740 |
| 4,857,716 | 8/1989 | Gombrich et al. | 235/462 |
| 5,344,666 | 9/1994 | Levine | 427/2.11 |
| 5,356,595 | 10/1994 | Kanamori et al. | 422/65 |

*Primary Examiner*—Harold Pyon
*Attorney, Agent, or Firm*—William H. Eilberg

[57] ABSTRACT

An automatic device prepares blood films or smears on microscope slides. The device has essentially one moving part, namely a carriage which holds the slide, and which is movable back and forth along a frame. The slide is dispensed from a magazine, onto the carriage, and the carriage moves to a position where a drop of blood is conveniently placed onto the slide. The carriage then moves to a position permitting contact between the blood and a spreading blade mounted on a flexible member. The carriage is moved in a forward direction, causing the blade to move relative to the slide, creating the blood smear. The slide is then lifted from the carriage and moved onto a storage platform. Meanwhile, the blade is cleaned as it passes over a cleaning pad on the carriage. Movement of the carriage in both directions insures that both sides and the end of the blade are cleaned. The device includes a bar code reader and printer, making it possible to read a bar code located on a specimen container, and to print indicia onto the slide, which may correspond to the coded information. The device also includes apparatus for automatically rejecting blank slides which have stuck together.

16 Claims, 11 Drawing Sheets

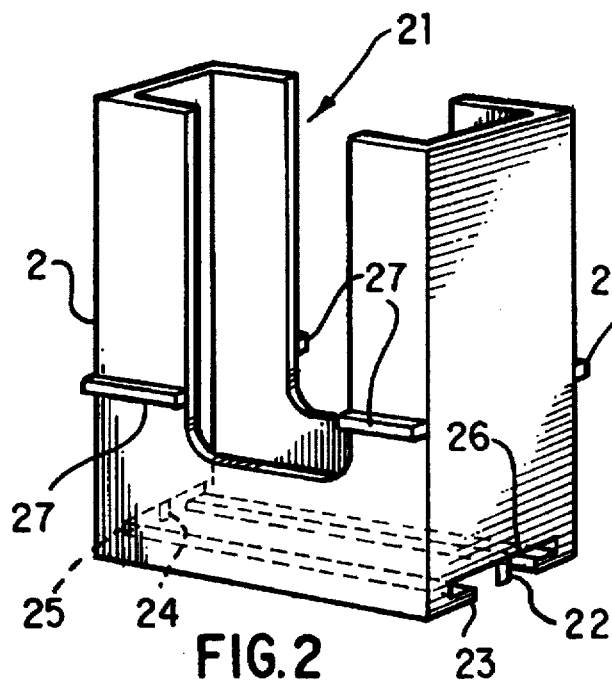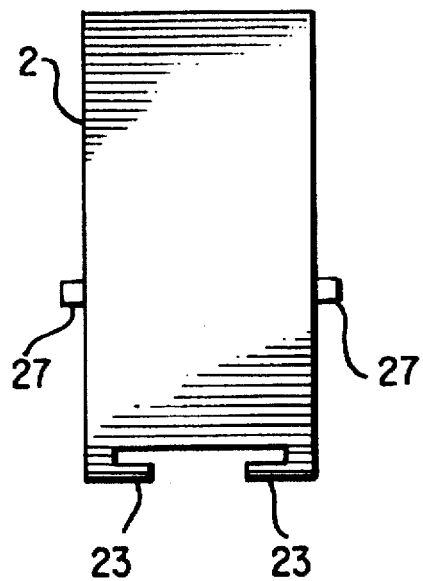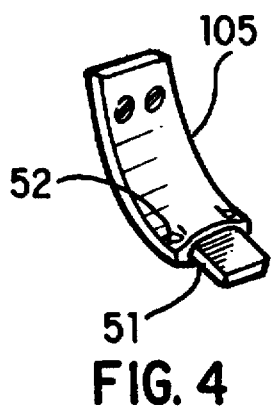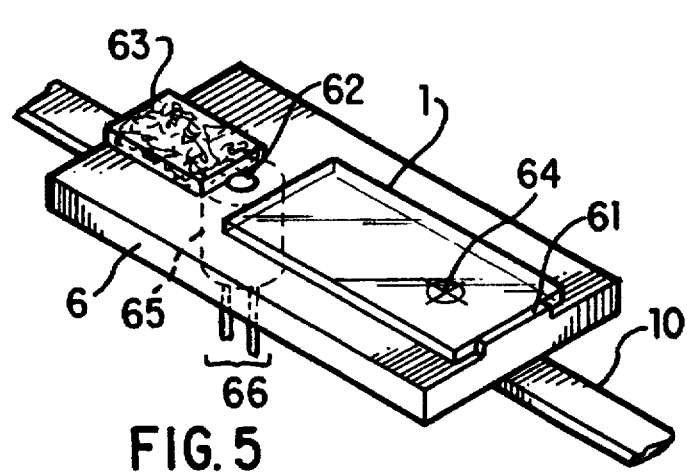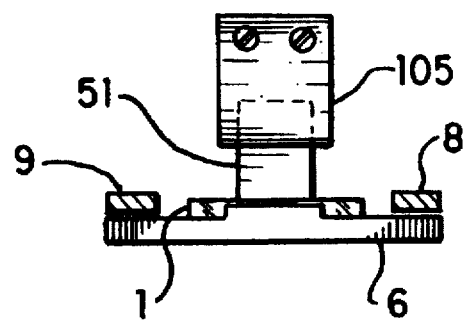

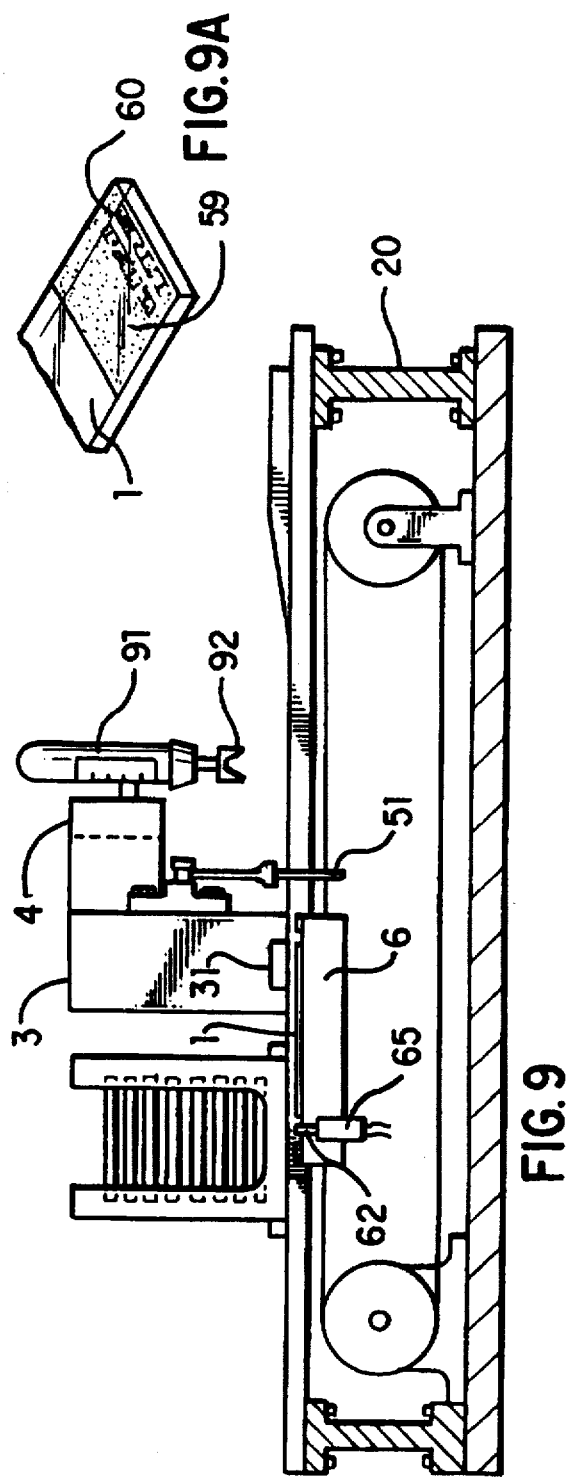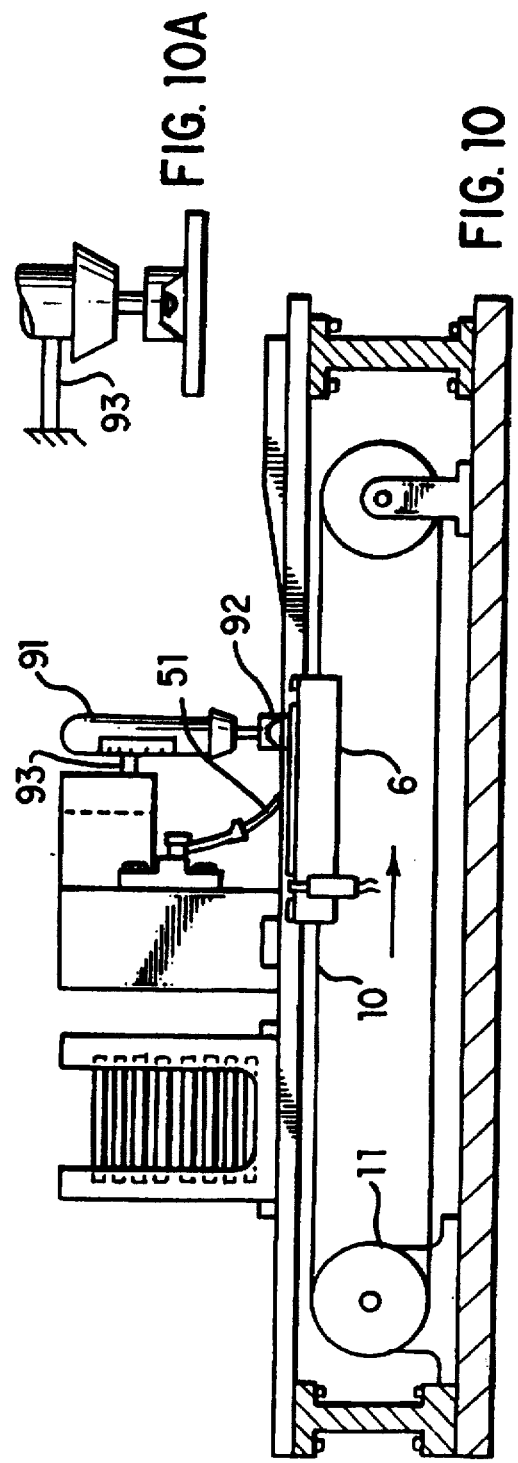

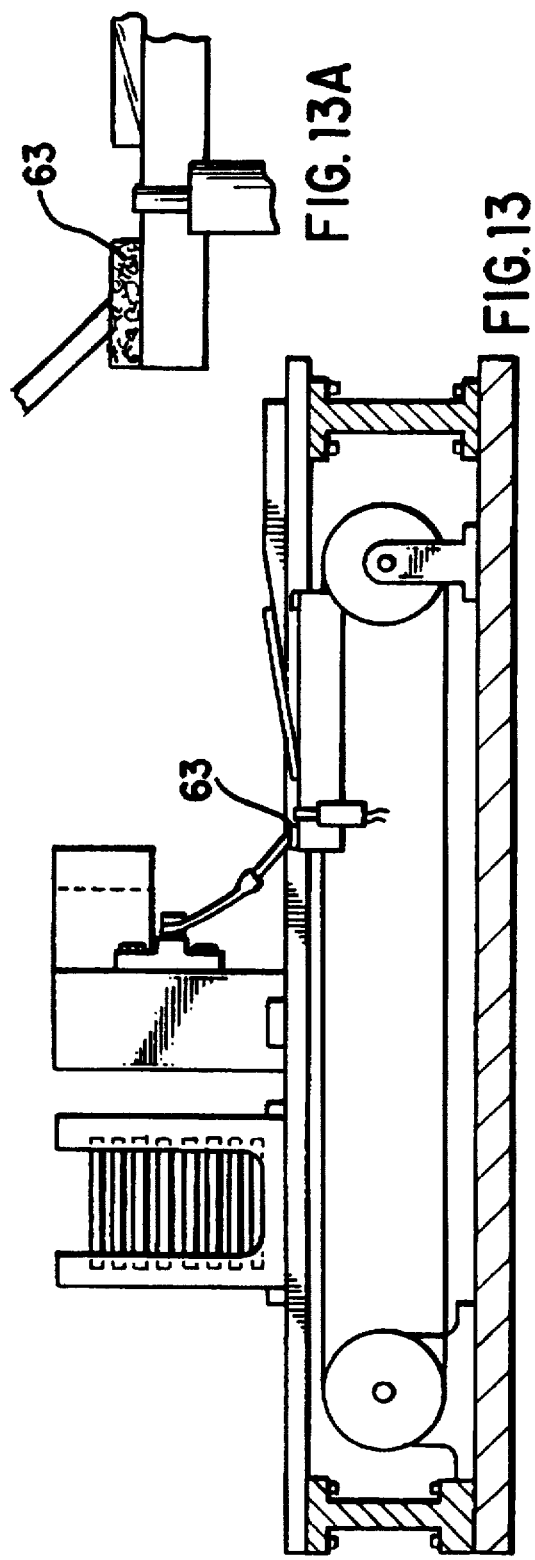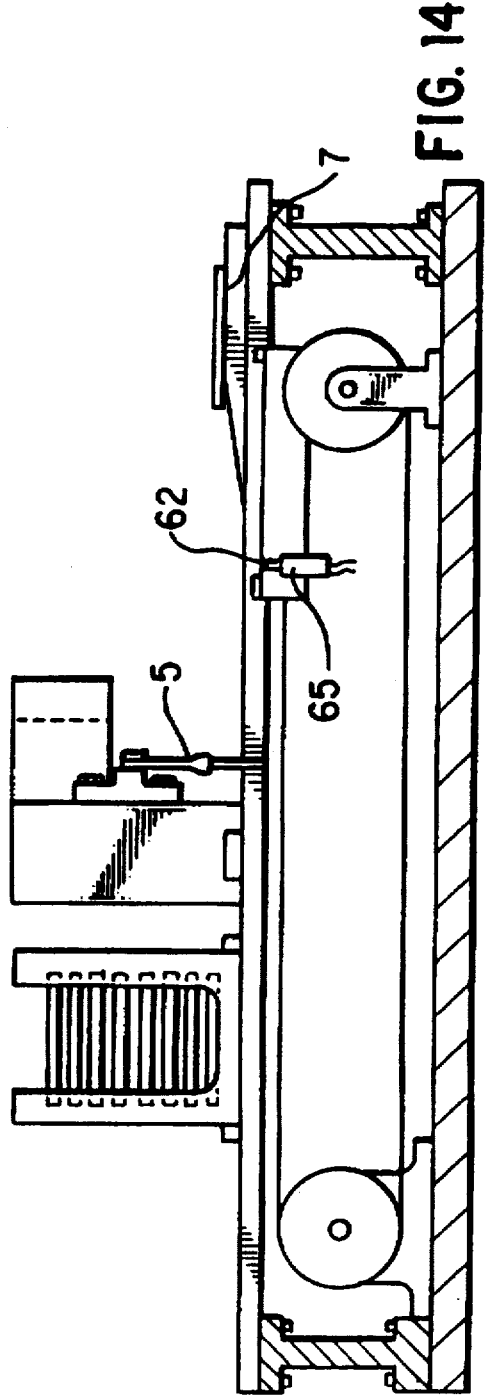

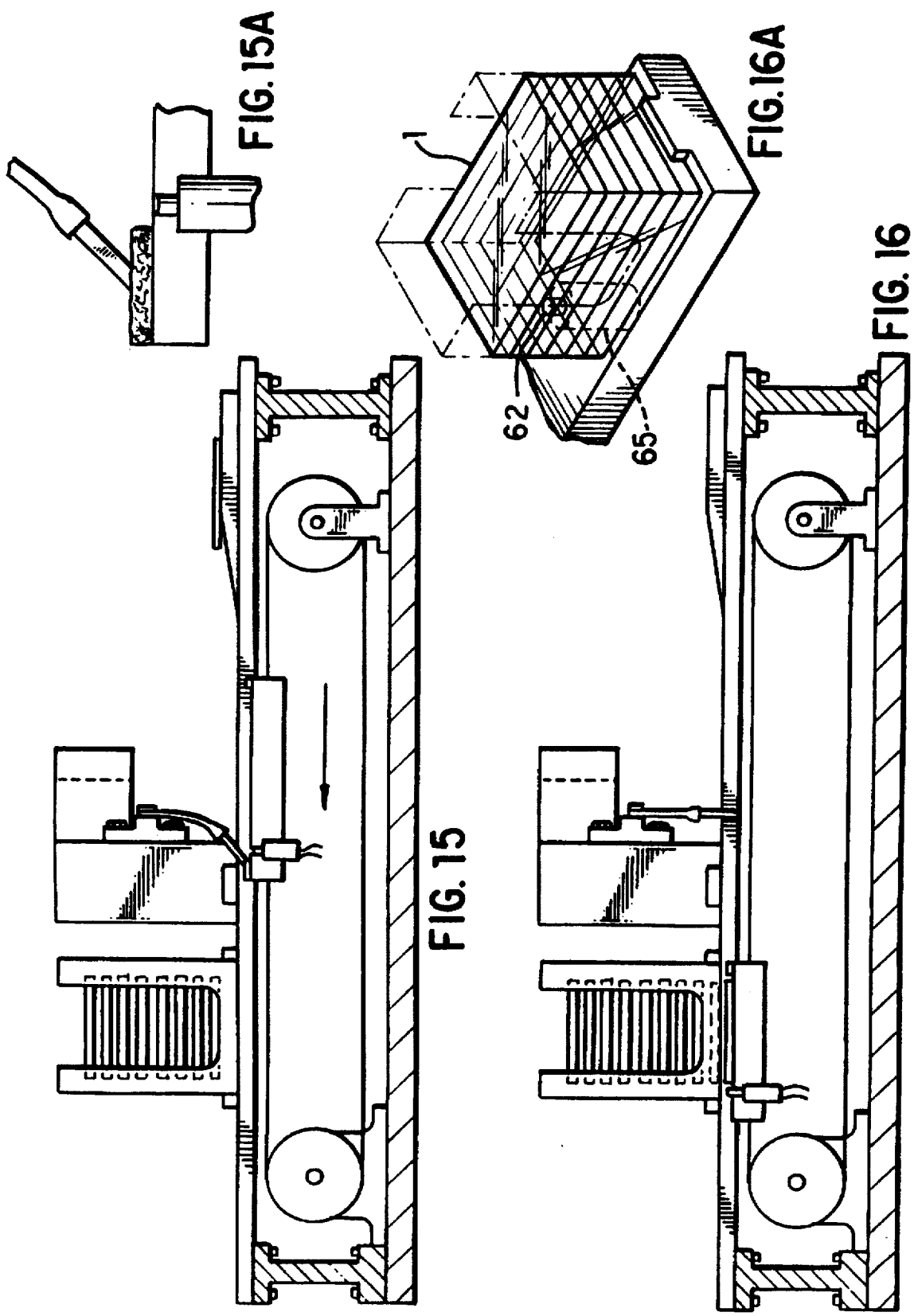

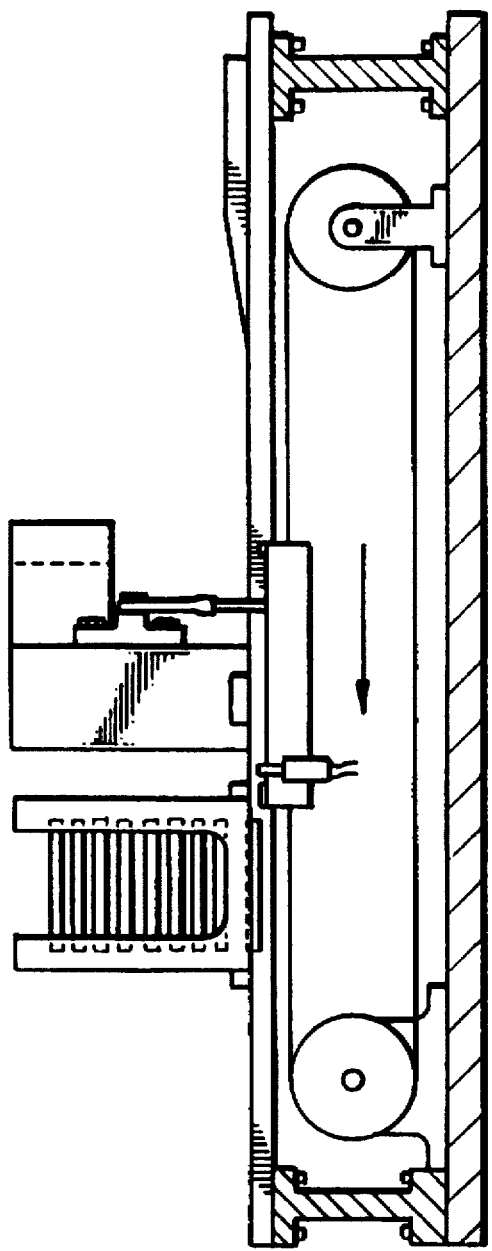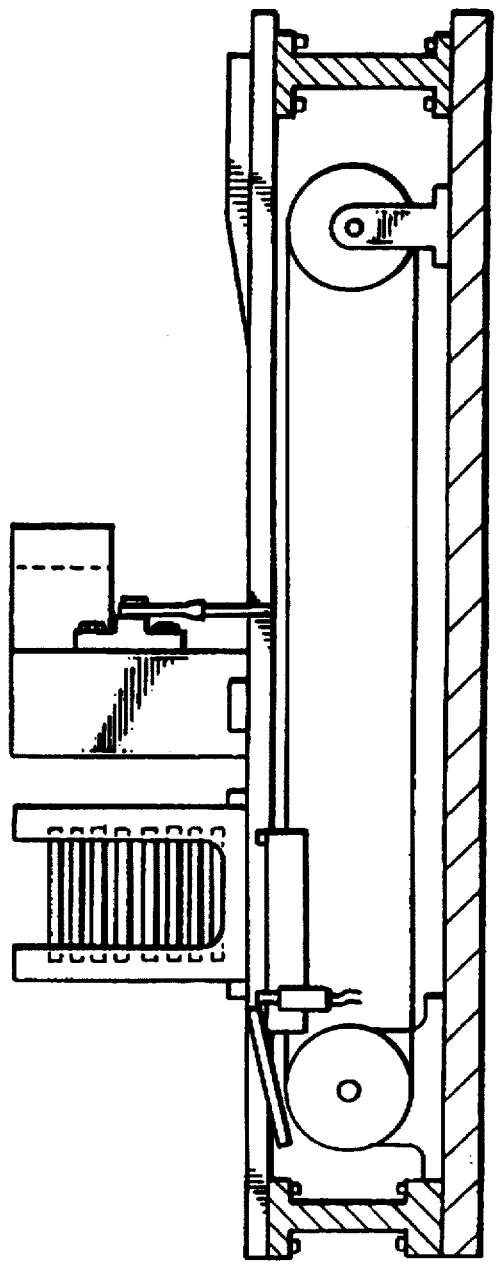

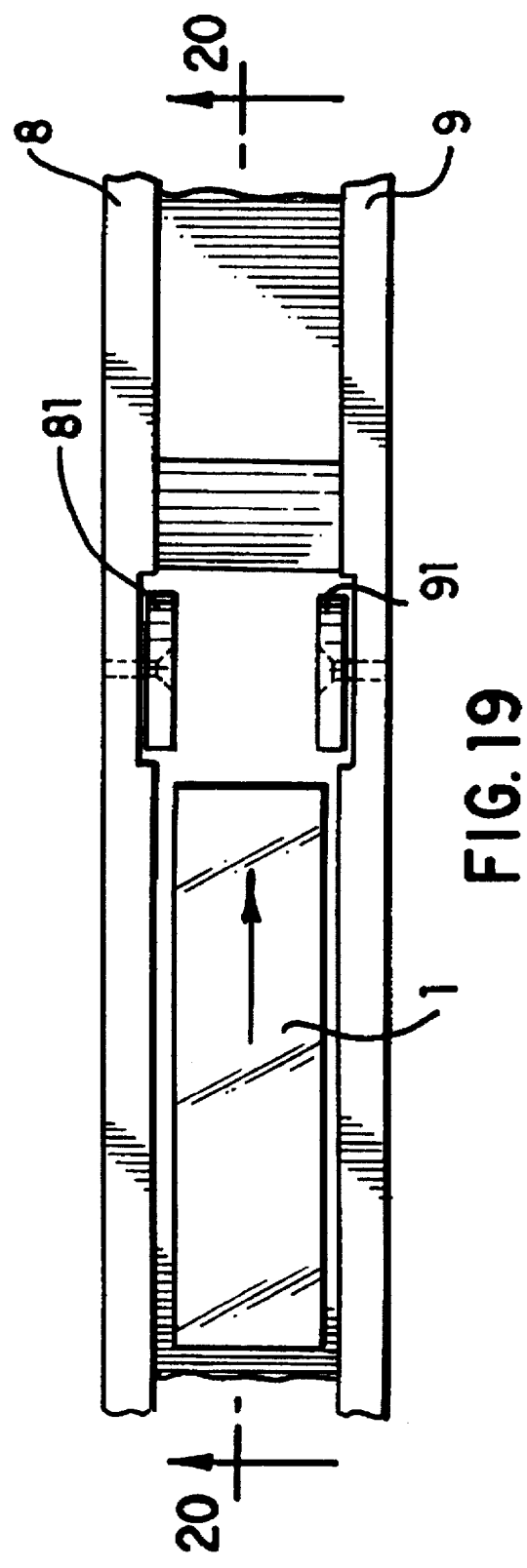
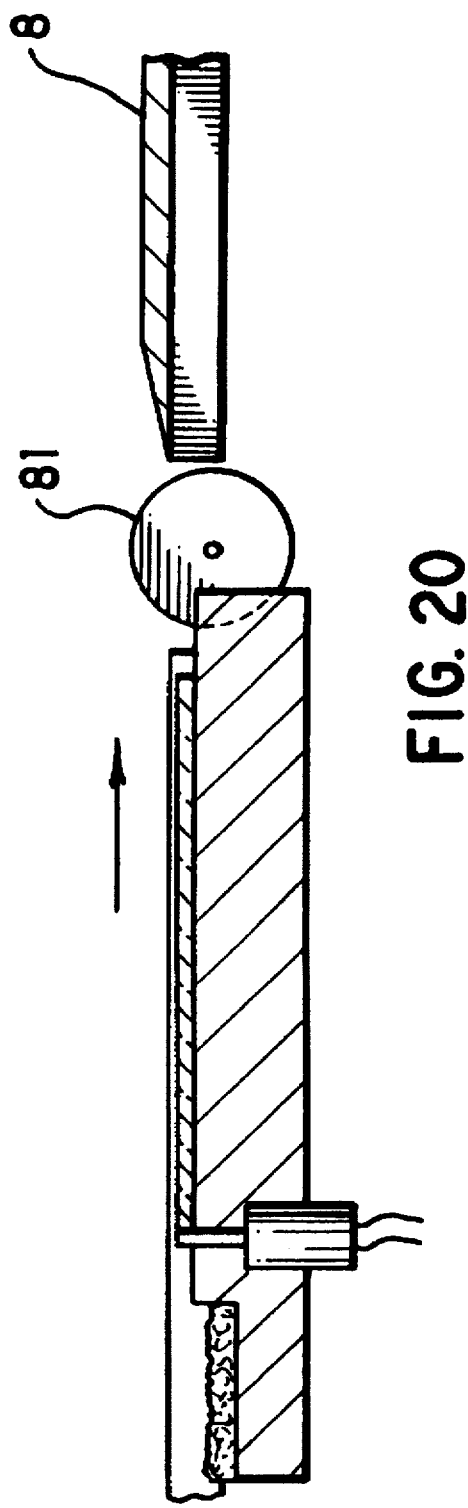
FIG. 19
FIG. 20

AUTOMATIC BLOOD FILM PREPARATION DEVICE

BACKGROUND OF THE INVENTION

This invention relates to the field of preparing slides of blood films for viewing under a microscope. The invention automates the entire process of smearing a drop of blood onto a slide.

A blood film or blood smear can be prepared manually, but to make the smear of the desired thickness, and with uniform thickness from slide to slide, considerable manual dexterity is required. Also, the preparation of blood smears can be quite time consuming. Thus, the industry has long sought a practical means of automating the preparation of blood smears.

The early attempts at automation have simply sought to mimic the manual techniques. In such early devices, a drop of blood was first deposited onto a glass microscope slide, and a glass spreader blade would engage the blood, causing it first to spread laterally across the slide. Then, a spreader, disposed at a fixed angle, would translate longitudinally along the slide at a controlled speed, pulling the blood behind it, and in so doing cause the blood to spread in decreasing thicknesses until the blood was completely smeared.

Early devices for automatic preparation of blood smears are disclosed in U.S. Pat. Nos. 4,151,915, 4,096,824, 4,061,108, and 3,880,111. The disclosures of the latter patents are hereby incorporated by reference into this specification. The prior art devices, as exemplified by the above-mentioned patents, sought to automate the process by providing both automatic smearing as well as automatic dispensing of a slide. However, the devices of the prior art have no means for cleaning the slide between preparations, and have no means of providing patient or specimen identification.

Since the introduction of the devices described above, other more automatic devices have been introduced, which include the above features but also add means for cleaning and for specie identification. However, such machines are complex and expensive. They require a multiplicity of independent stations needing multiple transfers of slide and specimen between stations in a robotic-like system.

Moreover, none of the devices known in the prior art provides means for solving the problem caused by slides which stick together, other than by stopping operation of the machine entirely, or by accessing a magazine of spare slides.

The present invention provides an automated apparatus which solves the problems described above, but which is relatively simple, relatively inexpensive, and compact.

SUMMARY OF THE INVENTION

The present invention is an automated instrument for preparing blood smears on microscope slides. The device includes essentially only one moving part, namely a carriage which moves back and forth along a frame. The carriage comprises means for supporting and transporting a slide. Mounted to the frame are a magazine for storing blank slides, a spreader assembly for spreading blood along the slide, and a ramp and platform for handling the slides after the blood smear is made.

The device preferably also includes a bar code reader, which interprets bar coded data on a test tube containing the specimen from which a smear is to be made, and a printer for printing indicia onto the slide, the indicia corresponding to the data read by the bar code reader.

The spreader assembly includes a flexible holding member, which has the form of a generally flat, thin, rectangular piece of flexible material, and a spreader blade, preferably made of thin glass, affixed to one end of the holding member. Due to the mounting of the holding member, and due to its inherent flexibility, the spreader assembly, including the blade, can swing freely back and forth, so that the blade can engage the surface of a slide conveyed by the carriage.

The carriage includes a cleaning pad, so that as the carriage approaches a position where the slide is to be removed from the carriage, the spreader blade contacts the cleaning pad and becomes cleaned before the next use. Movement of the carriage both forward and backward insures that both sides of the spreader blade are cleaned.

The invention also includes means for discarding slides when they stick together. The magazine that stores the slides contains a front opening and a rear opening. The front opening permits only one slide to pass through, and the rear opening is large enough to allow more than one slide to pass through. If the system determines that a pair of slides have stuck together (due to the failure of a slide to be dispensed normally through the front opening), the system is programmed to move the carriage rearward, so as to engage the stuck slides and push them out of the rear opening of the magazine.

The invention therefore has the primary object of providing an apparatus and method for automating the production of blood smears or blood films on microscope slides.

The invention has the further object of simplifying the hardware required for preparation of blood smears.

The invention has the further object of reducing the cost of preparation of blood smears.

The invention has the further object of providing an automated device for making blood smears, wherein the device requires a minimal amount of maintenance.

The invention has the further object of providing a device which automatically prepares blood smears, wherein the device is capable of detecting and discarding slides which have become stuck together, without requiring interruption of the operation of the device, and without requiring duplicate slide magazines.

The invention has the further object of providing apparatus for making a blood smear, wherein the apparatus is compatible with a device that draws blood from a closed tube without requiring that the tube be opened.

The invention has the further object of providing an apparatus for making a blood smear, wherein the apparatus includes means for insuring that a drop of blood is positioned at the proper location on a slide.

The invention has the further object of providing an apparatus as described above, wherein the apparatus occupies a relatively small amount of space.

The invention has the further object of providing an apparatus as described above, wherein the apparatus includes automatic means for cleaning a spreader blade between uses.

The invention has the further object of providing an apparatus as described above, wherein the apparatus includes means for reading a bar code located on a container which holds the specimen from which a smear is to be made.

The invention has the further object of providing an apparatus as described above, wherein the apparatus includes means for printing indicia onto a slide, said indicia corresponding to information represented by a bar code located on a container holding the specimen.

The invention has the further object of providing an apparatus as described above, wherein the apparatus includes means for communicating with a hospital or laboratory computer, to obtain information about the patient who supplied a particular specimen.

The invention has the further object of providing an apparatus as described above, wherein the apparatus includes a key pad for entering data and/or instructions into the apparatus.

The invention has the further object of providing an improved magazine for storing microscope slides.

The reader skilled in the art will recognize other objects and advantages of the invention, from a reading of the following brief description of the drawings, the detailed description of the invention, and the appended claims.

BRIEF DESCRIPTION OF THE DRAWINGS

FIG. 2 is a perspective view of the slide magazine used in the present invention.

FIG. 3 is an end view of the slide magazine of FIG. 2.

FIG. 4 is a perspective view of a portion of the spreader assembly used in the present invention.

FIG. 5 is a perspective view of the carriage used in the present invention, the view showing a slide in its location, and the location of the solenoid pin and the cleaning pad.

FIG. 6 is a cross-sectional end view showing the relationship of the spreader blade, the slide, and the rails, according to the present invention.

FIG. 9 is a side elevational view of the device of the present invention, the figure showing the carriage at the "home" position.

FIG. 9A is an inset of FIG. 9, showing, in perspective, an expanded view of the printing on the frosted or coated end of the slide.

FIG. 10 is a side elevational view, similar to that of FIG. 9, but showing the carriage at the location where blood is deposited on the slide.

FIG. 10A is an inset of FIG. 10, showing an expanded end view showing the depositing of blood onto a slide.

FIG. 13 is an elevational view similar to that of FIG. 9, showing the spreader being drawn across the cleaning pad, and showing at the same time that the slide is being pushed up the ramp.

FIG. 13A is an inset of FIG. 13, providing an expanded view showing the spreader being dragged across the cleaning pad at which time the face and back surfaces of the spreader are cleaned.

FIG. 14 is an elevational-view similar to that of FIG. 9, showing the slide having reached the top of the ramp and resting on the horizontal surface of the ramp.

FIG. 15 is an elevational view similar to that of FIG. 9, showing the carriage in reverse motion with the spreader being drawn across the cleaning pad in the reverse direction.

FIG. 15A is an inset of FIG. 15 showing the slide being drawn backwards across the cleaning pad as its front surface is being cleaned.

FIG. 16 is an elevational view similar to that of FIG. 9, showing the position of carriage under the magazine in preparation for dispensing a slide.

FIG. 16A is an inset of FIG. 16, and provides an expanded perspective view showing the pin of the solenoid in relationship to the bottom slide.

FIG. 17 is an elevational view similar to that of FIG. 9, and shows the carriage in position to reject stuck slides.

FIG. 18 is an elevational view similar to that of FIG. 9, and shows the stuck slides ejected out the rear of the magazine.

FIG. 19 provides a fragmentary top view of the device of the present invention, showing with the slide entering the ramp, and indicating the function of the rollers.

FIG. 20 provides a cross-sectional view, taken along the line 20—20 of FIG. 19.

DETAILED DESCRIPTION OF THE INVENTION

Figure 1:
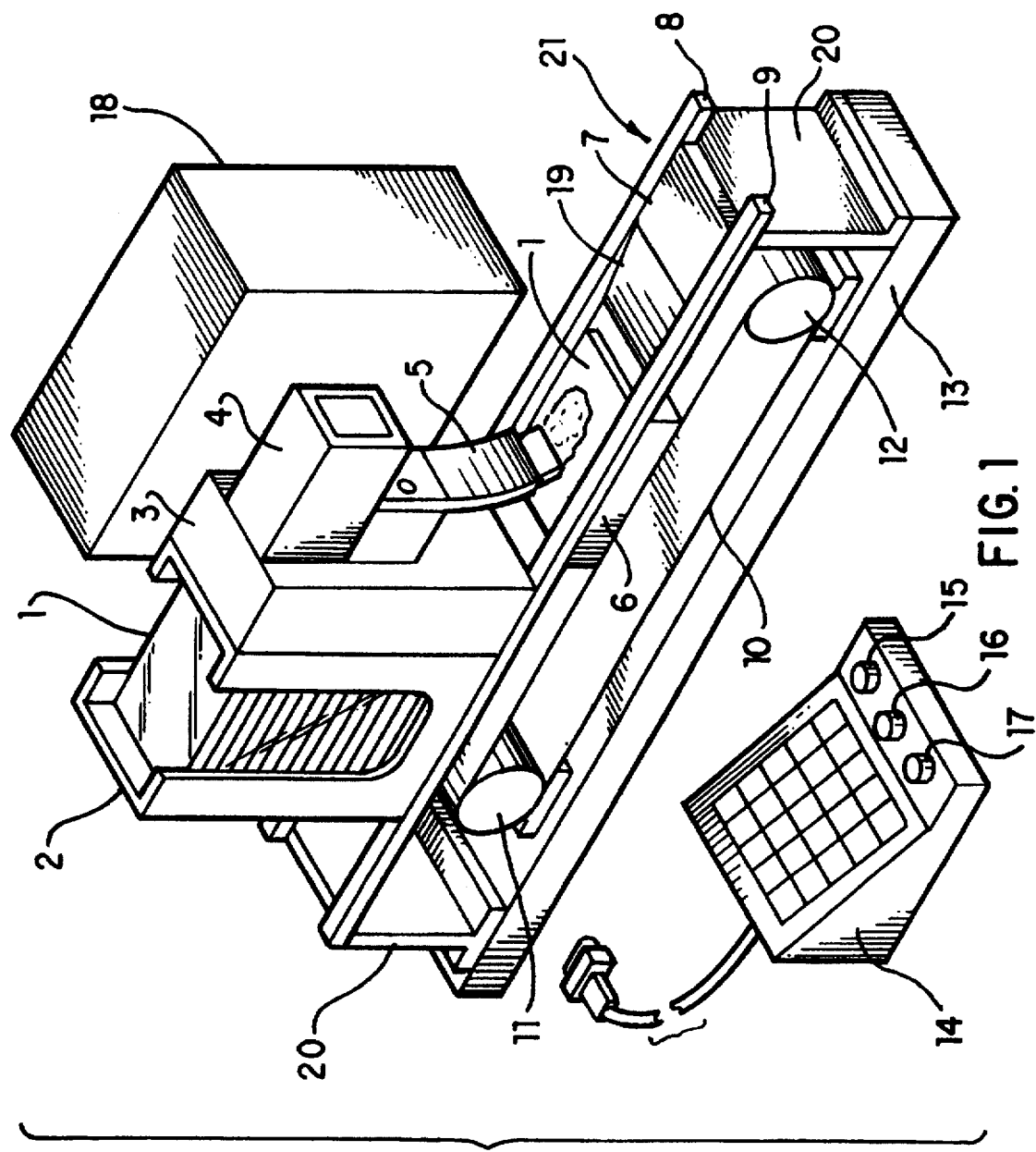
FIG. 1 is a perspective view of the device of the present invention, together with its optional key pad.

As shown in FIG. 1, the device of the present invention comprises the following major components. A magazine 2 contains slides 1. A printing unit 3 is used to print data onto slides. A bar code reader 4 reads data printed on a test tube, or other receptacle, containing a specimen from which a smear is to be made. A spreader assembly 5 spreads a blood sample along the surface of a slide. Carriage assembly 6 moves the slide in the desired manner. A drive belt 10, powered by motor 11, rotates idler pulley 12, so as to move the carriage. An exit ramp assembly 21 facilitates discharge of the prepared slides. The device is supported by stationary frame 20.

The system sits on base 13 which holds the frame. An optional keyboard includes actuation buttons 15, 16, 17 which select the speed of smearing, which may be either fast, medium, or slow, corresponding to the smearing rate requirements of blood of various viscosities. An electronics module 18 contains power supplies and computer elements, and may also contain an interface and connection to a laboratory computer.

FIG. 2 shows the structure of slide magazine 2. The magazine defines an open chamber where slides are housed and a front opening 26 which has a slot through which only one slide can pass, to dispense slides one at a time. A breakaway pin 22 is molded at the center of the opening to prevent inadvertent spilling of slides when the magazine is handled. This pin breaks away when the first slide is dispensed from the magazine. The breakaway pin thus functions as a keeping means, for holding the slides in place before the magazine is used. Alternatively, the breakaway pin could be replaced by a spring device.

The rear opening 25 is large enough to permit a plurality of slides to pass and is used for rejecting stuck slides, as described later. A breakaway pin 24 is molded in the center of the opening to prevent inadvertent spilling of slides during handling of the magazine. The pin breaks away when stuck slides are forced out the rear as will be discussed below.

Magazine 2 contains shelves 23 which extend along the underside of the magazine to support the slides. The deep openings in the sides of the chamber permit easy handling of slides during loading. The shelves 23 are more clearly visible in the end view of FIG. 3. The magazine may also contain ledges 27 which extend along its sides, as shown in FIGS. 2 and 3. The ledges makes it easier to position the magazine relative to the frame by providing an additional supporting surface.

Although not shown in FIGS. 1—3, the magazine also preferably includes a foam spacer, inserted over the top slide. The spacer may be a rectangular piece of foam, or other soft and flexible material, sized to conform to the space defined by the magazine, and having a thickness equal to that of one or more slides. A piece of tape, or equivalent retaining means, can be affixed across the top of the spacer to prevent slides from falling out of the top when the magazine is stored and transported.

FIG. 4 shows more detail of the structure of the spreader assembly 5. The spreader assembly comprises a compliant holding member 105 with socket 52 and spreader blade 51. Socket 52 is shown in more detail in FIG. 7. The blade is typically about one mm thick and is about three-fourths the width of a slide. It is held in place in the socket either by press-fitting or with the assistance of screws 52. The holding member 105 acts as a flat spring which is free to be deformed in both the forward direction during smearing, as shown, or in the reverse direction, during cleaning of the spreader blade, as will be described below. In either direction, deformation of the spring causes a downward pressure, which in the case of smearing causes the edge of the spreader blade to rest firmly against the microscope glass, thus preventing blood from undesirably being sucked underneath the edge of the spreader.

The holding member also can twist back and forth. Indeed, one can describe the holding member as capable of essentially universal movement. Thus, if the slides have non-uniformities, or if there are slight variations in the positioning of the slides, all of the spreader blade will still make contact with the slide. Moreover, the present invention accomplishes the goal of insuring full contact between the blade and the slide, without requiring any more complex machinery than the flexible holding member.

FIG. 5 shows the carriage assembly 6 which includes solenoid 65 with pin 62 and wires 66. Front tab 61 and replaceable cleaning pad 63 are also shown. Slide 1 is prevented from moving along the longitudinal axis of the carriage by the elements 61 and 62. A reference mark 64 is located on the top surface of the carriage and is visible through the slide. The mark 64 indicates the location where the blood drop is to be placed and also indicates the required size of the blood drop. Belt 10 is attached to the carriage and provides motion in both directions as will be explained below.

FIG. 6 shows the relationship of slide 1 and rails 8 and 9, which hold the slide in the desired position on the carriage.

For clarity of illustration, rails 8 and 9 were not shown in FIG. 5. The slide travels while resting on the carriage 6, and the rails prevent the slide from moving laterally. The spreader blade covers only part of the width of the slide. The latter feature has the benefit that both edges of the blood smear can thus be seen under a microscope, without distortion due to the edge of the slide. Rails 8 and 9, in conjunction with ledges 27, can also serve the purpose of providing a secure mounting for the magazine on the frame, and the magazine can be provided with suitable means for engaging the rails.

The preferred material for the spreader blade is glass, because glass has a high surface tension. Unlike the holding member 105 which is flexible, the blade itself does not flex. The blade can be made of other materials, within the scope of the invention.

Figure 7:
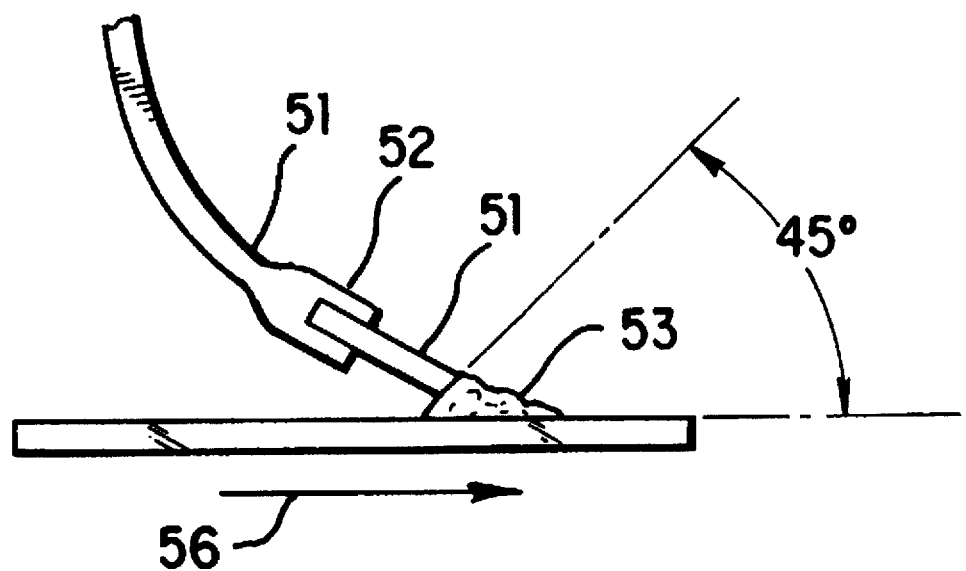
FIG. 7 is a side elevational view of the spreader of the present invention, in the process of smearing blood along the slide.

FIG. 7 shows the relationship between the spreader blade 53 and the slide. The spreader blade presents its forward edge to the blood drop at an angle of approximately 45 degrees relative to the surface of the slide. The glass blade of the spreader provides surface tension which pulls the blood along as the slide moves along the direction indicated by arrow 56, due to the motion of the carriage.

The speed of the carriage is selected on the keyboard, as described above. It is well known that slow motion thins the smear; slow motion is used when the blood has high hematocrid, i.e. a large fraction of cells in a given liquid volume. Fast motion thickens the smear and is used when the blood has low hematocrid. As the blood is drawn along the slide, the cross-section of the smear is wedge-like, with the thickest part at the beginning and the thin area at the end. It is the thin area that is preferable for viewing with a microscope.

Figure 8:
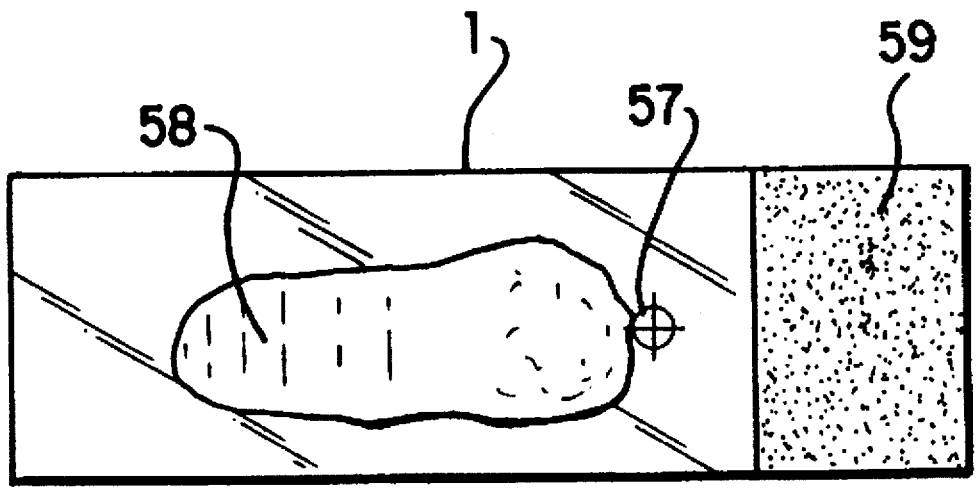
FIG. 8 is a top view of a slide with blood film smear, as used in the present invention.

The top view of FIG. 8 shows the shape of the smear, the beginning of the smear being indicated by reference numeral 57, where the drop of blood is deposited, and the end of the smear being indicated by reference numeral 58, where the smear forms a fine edge. The slide typically is partially frosted or coated at 59, which provides a surface suitable for printing.

FIG. 9 illustrates the use and operation of the device of the present invention. FIG. 9 shows carriage 6 in its home position, which is beneath the printing unit 3, where the slide is sheltered from dust while waiting to be used. At this time, the solenoid pin 62 is in the raised position. The spreader assembly is shown in the neutral position at which the spreader blade is pointing downward and is not in contact with any member. At this time, a test tube 91 containing blood is positioned in front of the bar code reader 4. The test tube typically used is the well-known Vacutainer brand which has been filled with blood from the patient, and a bar code label providing specimen identification has been adhered to the tube. Other data on the label may typically include the patient's name and billing number.

The bar code on the test tube is transformed into a numerical value by the computer, and the printing head 31 of printer 3 records the numerical value and/or other information onto the forward portion of the slide where, as described above, the frosting or coating is located. FIG. 9A provides an enlarged view of the forward portion of the slide, showing the data having been printed onto the slide.

As illustrated by FIG. 10, the carriage is automatically driven by the motor 11 and belt 10, at slew speed, to the next position where the blood is to be deposited onto the slide at the target area. The drive system uses a popular stepping motor either with a belt drive, as shown, or with a linear stepping motor. The motor is programmed to move at various speeds, and to stop at locations determined by counting a prescribed number of pulses corresponding to the number of increments between locations. In addition, the system includes backup detectors comprising photocells, which sense when the carriage has reached critical locations. The photocells verify the locations in case the count of the stepping system is in error. The rate of pulses determines the speed of motion of the carriage, which must be selected according to the smearing speed desired.

Other drive systems are also acceptable, such as a belt or wire drive with a DC motor, working in conjunction with photocells or limit switches. Here too, the photocells verify that the carriage has reached a particular position. In cases where various speeds are required, as in smearing, which will be discussed below, the voltage of the DC motor is varied to accommodate the requirement.

In order to facilitate the placement of the blood, a guide bar 93 facilitates the positioning of the test tube. The test tube is agitated to achieve good mixing of blood before the blood is sampled by the device. The drop of blood is preferably obtained through the use of a blood dispenser of the type described in U.S. Pat. No. 5,344,666, the disclosure of which is hereby incorporated by reference into this specification. The device described in the latter patent insures that the drop of blood will be of the proper size, and makes it possible to transfer the blood quickly without opening the stopper of the test tube. The latter device is shown in more detail in the expanded view of FIG. 10A. The latter device is manually operated to dispense the desired drop of blood onto the slide.

As an alternative to using the device described in U.S. Pat. No. 5,344,666, one can use a pipet, or capillary tube, or a stick, such as is commercially available. As another alternative, one could provide a permanent conduit or tube, leading from a blood storage means, to the vicinity of the slide, to dispense the drops. The invention is not limited to a particular means of delivering the blood. In all of the latter alternatives, one needs to remove the stopper of the test tube. Also, when using the latter alternatives, the mark 64, described above, provides indication of the proper location and the diameter of the mark indicates the size of the desired drop. But when the device shown in U.S. Pat. No. 5,344,666 is used, in conjunction with guide bar 93, the mark is not necessary, as the guide bar assures proper placement of the droplet.

Figure 11A:
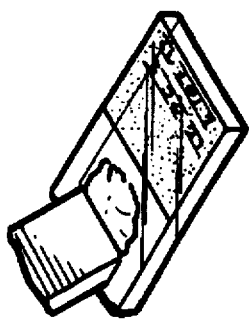
FIG. 11A is an inset of FIG. 11, providing an expanded perspective view showing the spreader in the process of engaging with the blood drop.
Figure 11:
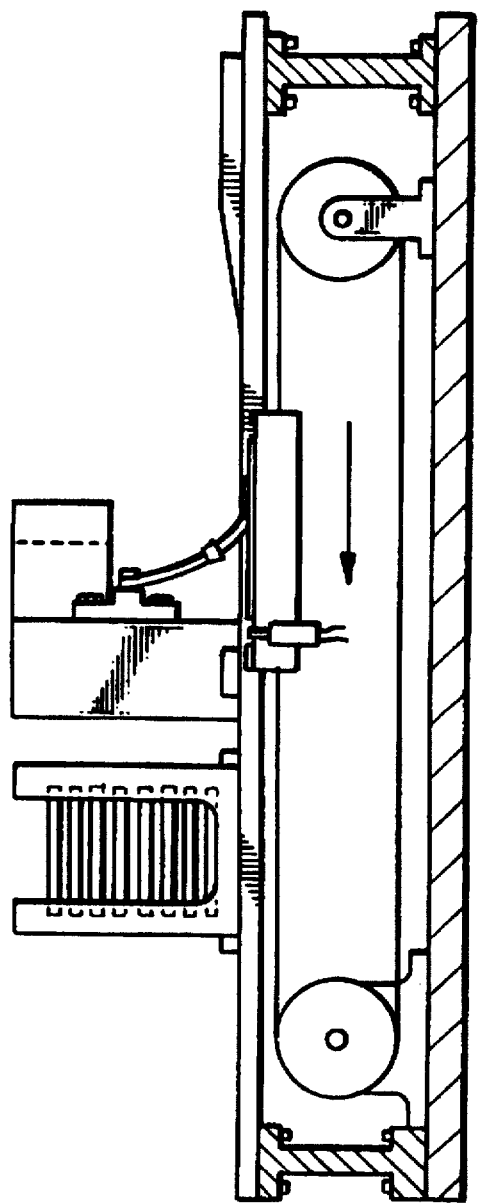
FIG. 11 is an elevational view similar to that of FIG. 9, showing the carriage at the position where the spreader blade picks up blood.

Next, as shown in FIG. 11, the carriage is driven backwards at a slow speed, as indicated by the arrow. The slide is pushed backwards by tab 61, which engages the slide. As the slide is pushed backwards, the spreader blade, which is stationary relative to the frame, moves forward along the slide, and comes into contact with the blood drop. The location of the drop is known to the system since the blood was originally automatically placed at the prescribed location, as described above.

When the spreader engages the drop of blood, the motion of the spreader is automatically stopped for about 1–2 seconds to allow the blood to spread laterally until the blood reaches full width on both sides of the spreader. This effect is well-known and is caused by capillary action in the 45-degree angular trough formed between the spreader and the slide, as described above. The expanded view of FIG. 11A provides more detail of the relationship between the spreader blade and the slide.

Figure 12A:
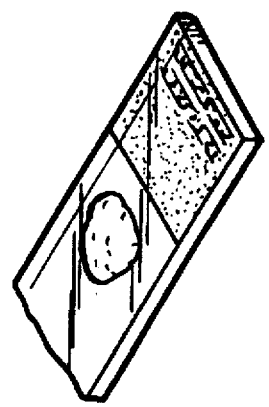
FIG. 12A is an inset of FIG. 12, showing an expanded perspective view of the blood smear.
Figure 12:
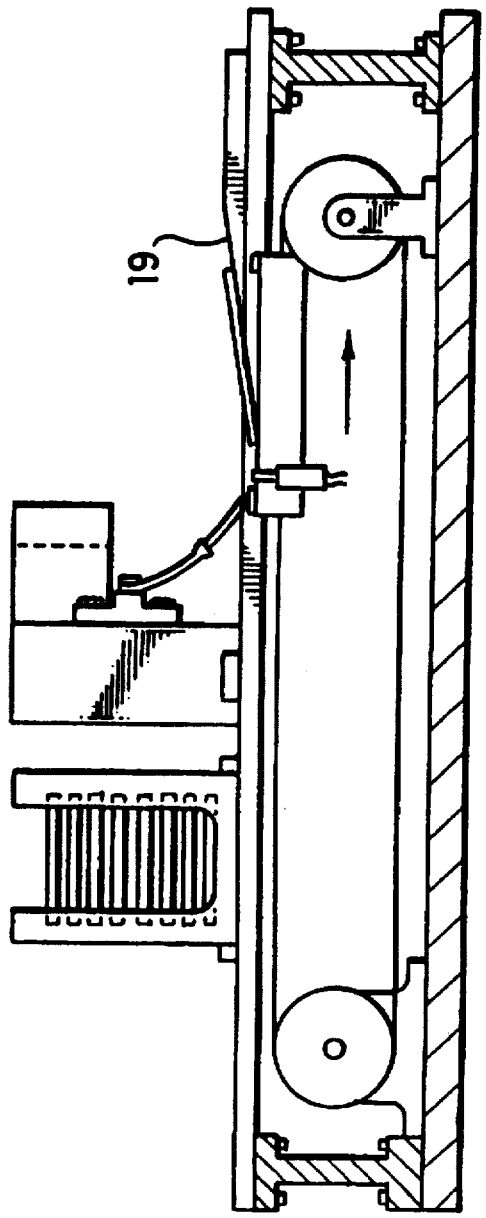
FIG. 12 is an elevational view similar to that of FIG. 9, showing the blood being spread as the carriage moves.

The blood is spread along the slide as the carriage moves towards the right, as shown in FIG. 12. Since the spreader blade is stationary relative to the frame of the device, and since the slide moves with the carriage, to the right, the blade is dragged to the left relative to the slide, spreading the blood over the slide. The blood is pulled along the slide by the spreader blade, due to the attraction, by surface tension, between the blood and the surface of the slide. When the carriage has advanced so far that the blade approaches the end of the slide, the slide begins to travel up ramp 19.

The speed at which the carriage moves has been selected by buttons 15, 16, 17 on the keyboard, as described above. These speeds range from approximately 1 to 2 inches per second. This range can be readjusted by the user by programming codes on the keyboard or by a variable resistor, not shown, the value of which is automatically interpreted by the computer. As is well-known from conventional manual methods of preparation of blood smears, a fast speed produces a shorter and thicker smear, while a slow speed produces a longer and thinner smear.

The expanded perspective view of FIG. 12A shows the shape of the smear relative to the features of the microscope slide. The smear begins after the frosted portion, which has indicia imprinted thereon, and continues to nearly the end of the slide where the thinnest portion of the smear is formed. Along the way, the smear is kept from reaching fully to the edges of the slide, as described above.

It is not desirable for the smear to extend completely to the end of the slide. The initial blood pick-up procedure prevents the latter from happening. After the blood is spread laterally, as described above, the initial motion of the spreader relative to the glass, during motion of the carriage, causes excess blood to spill before the remainder of the blood is spread. This is because the surface tension between the blood and the glass is only able to maintain a certain amount of attraction. Only the blood in direct contact with the spreader is drawn forward, while any excess is, in effect, dumped onto the slide. The latter excess is located at the initial portion of the smear, which will be ignored during analysis of the smear.

The carriage continues to move to the right, driving the slide up the ramp, as shown in FIG. 13. As shown in FIG. 13, the slide has advanced beyond the spreader blade, and the blade is drawn across cleaning pad 63. The purpose of the ramp is to lift the slide above the carriage so that the carriage can be withdrawn without carrying the slide back during the return trip of the carriage.

Figure 23:
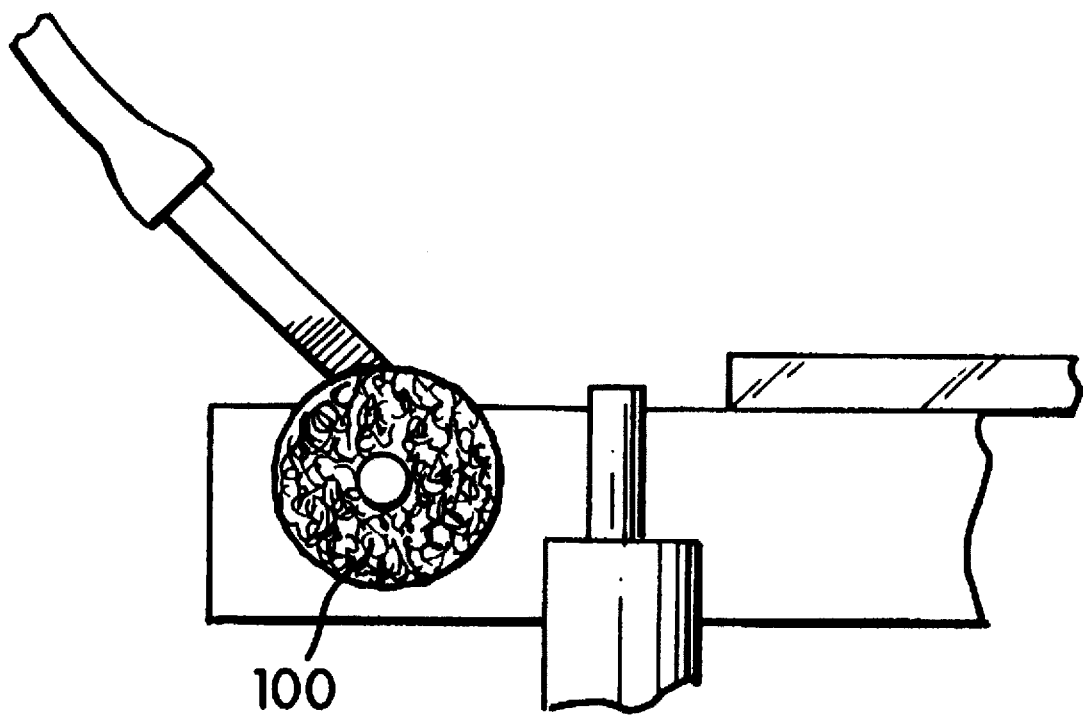
FIG. 23 provides a diagram similar to FIG. 13A, showing the embodiment in which the cleaning pad is replaced by a cleaning roller.

The expanded view of FIG. 13A shows the spreader blade as it is drawn over the cleaning pad. The spreader blade continues to exert downward spring force while it traverses the cleaning pad. Any blood which may have remained after smearing, on the back and bottom surfaces of the spreader, is immediately wiped off, before any blood can adhere to such surfaces. The cleaning pad is typically dry, but can be slightly moist. The pad preferably has a sticky bottom surface, and can be periodically replaced. In an alternative embodiment, the cleaning pad could be replaced by a roller or a continuous tape, which indexes to a new position with each use. In the latter arrangement, the system would always provide a fresh surface for cleaning. The roller or tape would then be replaced when all of its surface area had been used. FIG. 23 provides a diagram, similar to FIG. 13A showing this alternative embodiment, wherein the cleaning pad is replaced by cleaning roller 100.

In FIG. 14, the slide has been moved fully up the ramp, until its center of mass causes it to come to rest on platform 7, which comprises a horizontal surface adjacent to the ramp. Note that the spreader assembly falls off the end of the cleaning pad, which is affixed to the movable carriage, and rests in its neutral position defined above. FIG. 14 shows the spreader assembly in this neutral position. At this time, pin 62 of solenoid 65 is retracted, and the carriage immediately begins its return to the left.

As the carriage retracts, moving to the left, the spreader assembly is bent backwards, as shown in FIG. 15. The expanded view of FIG. 15A shows the spreader blade being dragged backwards over the cleaning pad. At this time, the bottom edge and forward surface of the blade comes in contact with the pad and is cleaned, thus removing any blood which may remain from the smearing operation. This final cleaning occurs so rapidly after the smearing that the blood does not have an opportunity to dry and adhere.

FIG. 16 shows the carriage in position to dispense the next slide from the magazine. At this time, the solenoid pin is raised and the carriage moves in the forward direction, i.e. to the right in FIG. 16. Initially, the first slide dispensed from a new magazine causes pin 22 to break away.

The expanded perspective view of FIG. 16A-shows the solenoid pin 62 in relationship to the slide in the magazine. The solenoid pin is raised to a few thousandths of an inch below the top surface of the lowest slide, so that the slide above the lowest slide is not affected.

In the event that any slides are stuck together, the system monitors whether the slide is dispensed from the magazine in the time expected, by sensing any excess time required for the carriage to reach the "home position" or otherwise by sensing when excess force or energy is required by the drive system. If slides are stuck together, the pair is prevented from exiting the magazine, since the forward opening will only allow passage of only one slide at a time.

The system solves the problem of stuck slides in the following way. First, the system retracts the solenoid pin and moves the carriage to a forward location, as shown in FIG. 17. The solenoid pin is raised in front of the slide. Next, the carriage moves in the reverse direction, to the left in FIG. 17, forcing the stuck slides out the rear opening of the magazine. During ejection, pin 24, as described above, is forced to break away by the exiting slides. As shown in FIG. 18, the stuck slides have been ejected from the rear of the magazine, having been pushed by the solenoid pin. The opening at the rear of the magazine must be larger than the opening at the front; only one slide at a time is permitted to exit the opening at the front, but groups of stuck slides are ejected through the opening at the rear. Then, the carriage engages the next slide, and with the pin remaining in the raised position, the carriage moves in the forward direction (to the right in the figures) to dispense the next slide.

Details of the slide ramp are shown in the top view of FIG. 19. Rails 8 and 9 contain rollers 81 and 91 respectively. The slide 1 is shown moving forward, due to the motion of the carriage supporting the slide. The side elevational view of FIG. 20 shows the slide approaching wheel 81 of rail 8.

Figure 21:
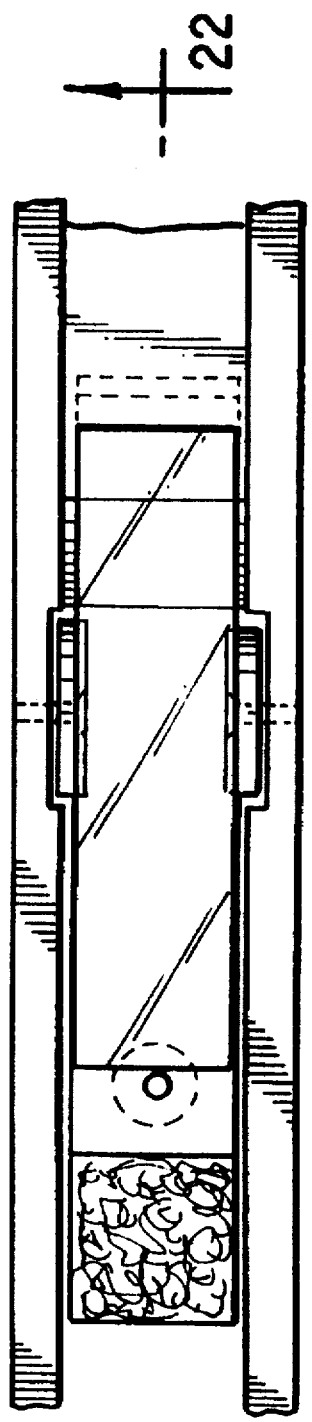
FIG. 21 provides a fragmentary top view of the device of the present invention, showing the slide having been tilted up the ramp by the rollers.
Figure 22:
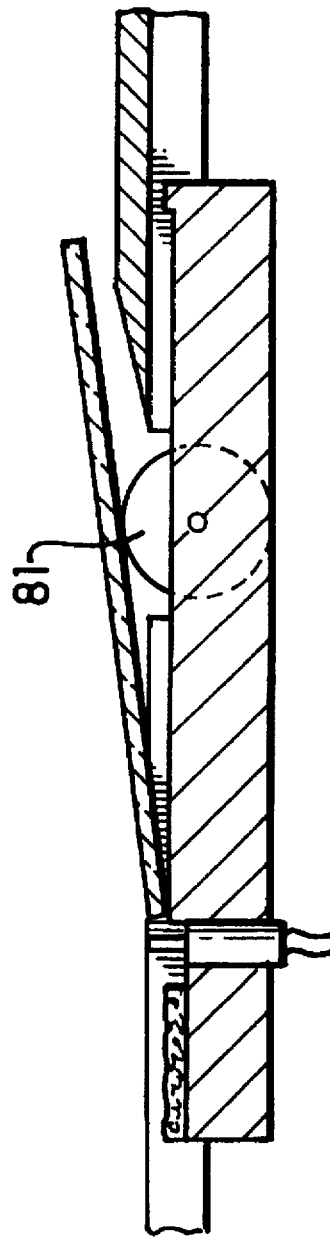
FIG. 22 provides a cross-sectional view, taken along the line 22—22 of FIG. 21.

FIGS. 21 and 22 show the condition wherein the slide has been angularly raised by rollers 81 and 91. Since the rollers rotate slightly when the sharp edge of the slide comes in contact with the rollers, nicking of the rollers is minimized. Also, the lifting of the slide by the rollers tends to prevent damage to the ramp due to the sharp edges of the slide. The rollers could be eliminated, but in the latter case, the ramp should be made of a hardened material that resists nicking.

The electronics module 18 may also include a communication interface between a microprocessor housed in module 18 and a computer housed in the laboratory or hospital. In this way, information about the patient, stored in the hospital or laboratory computer, can be retrieved by the present system, based on the data read from the bar code.

One can use a two-dimensional bar code on the test tubes or receptacles used with the device of the present invention. A two-dimensional bar code is known in the art. With a two-dimensional bar code, it may be possible to eliminate the need to provide an interface with the laboratory computer, because more information could be stored on the test tube.

The computer can also be programmed to keep a record of the date, and the apparatus can be programmed to print the date onto the slide, in addition to other indicia described above.

The present invention can be modified in various other ways, as will be apparent to those skilled in the art. Such modifications should be considered within the spirit and scope of the following claims.

What is claimed is:

1. An apparatus for automatic preparation of a blood smear on a slide, the apparatus comprising:
   a) a stationary frame,
   b) a carriage mounted on the frame, and means for moving the carriage back and forth along the frame, the carriage having means for holding a slide such that movement of the carriage causes movement of the slide, and
   c) means for spreading a drop of blood along the slide, the spreading means being attached to the frame, the spreading means comprising an elastically bendable member which can sway in both a forward and a backward direction,
   wherein the elastically bendable member has a distal end, and wherein there is a spreader blade mounted at said distal end,
   and wherein the cleaning means comprises a cleaning pad mounted on the carriage, and wherein the spreading means is capable of engaging the cleaning pad both in the forward and backward directions, wherein the cleaning means comprises means for cleaning both sides of the spreading means.

2. The apparatus of claim 1, wherein the cleaning pad is adhesively attached to the carriage.

3. The apparatus of claim 1, further comprising bar code reader means and printing means, the bar code reader means and the printing means being attached to the frame, the bar code reader means comprising means for reading a bar code located on a test tube, the printing means comprising means for printing indicia onto the slide, wherein the indicia correspond to information contained in the bar code.

4. The apparatus of claim 1, further comprising programmable means for storing a date, and means for printing a date onto the slide, the printing means and programmable means being attached to the frame.

5. The apparatus of claim 1, wherein the apparatus includes means for sheltering the carriage when the apparatus is not in use.

6. The apparatus of claim 1, further comprising a programmed computer, the computer being programmed to control movement of the carriage.

7. The apparatus of claim 6, wherein the computer stores information about various patients, the computer being connected to the printing means, wherein the computer comprises means for determining information to be printed onto the slide.

8. The apparatus of claim 6, further comprising a keyboard which is connected to the computer, the keyboard comprising means for transmitting information to the computer.

9. The apparatus of claim 1, further comprising ramp means for conveying a slide containing a blood smear to a platform, the ramp means and the platform being mounted on the frame, the platform being distinct from the carriage, wherein movement of the carriage does not affect a slide stored on the platform.

10. The apparatus of claim 9, wherein the ramp means includes rollers for moving, the slide towards the platform.

11. The apparatus of claim 10, wherein the rollers comprise means for lifting the slide as it is being moved toward the platform.

12. An apparatus for automatic preparation of a blood smear on a slide, the apparatus comprising:
   a) stationary frame,
   b) a carriage mounted on the frame, and means for moving the carriage back and forth along the frame, the carriage having means for holding a slide such that movement of the carriage causes movement of the slide, and
   c) means for spreading a drop of blood along the slide, the spreading means being attached to the frame, the spreading means comprising an elastically bendable member which can sway in both a forward and a backward direction,
   wherein the carriage includes means for cleaning the spreading means after the blood smear is prepared,
   and wherein the cleaning means comprises a roller, the roller being mounted to the carriage and being in sufficient proximity to the spreading means to allow the spreading means to contact the roller.

13. Apparatus for automatic preparation of a blood smear on a slide, the apparatus comprising supply means for holding a plurality of blank slides, spreading means for spreading a drop of blood along a slide, the spreading means comprising an elastically bendable member terminating in a blade, the bendable member being movable back and forth relative to a surface of a slide, wherein the blade engages the surface of the slide, the apparatus further comprising storage means for depositing slides which contain blood smears, all of the supply means and spreading means and depositing means being connected to a stationary frame, the apparatus also comprising a carriage which is movable relative to the frame, the carriage comprising means for holding a slide, the carriage being capable of moving sufficiently near the spreading means such that the spreading means engages a slide on the carriage, wherein the carriage includes a cleaning pad, the cleaning pad comprising means for cleaning the blade after the blood smear is prepared, the cleaning pad being mounted to the carriage and movable therewith.

14. The apparatus of claim 13, wherein the supply means includes two oppositely-directed openings, wherein one of said openings permits passage of only one slide, and wherein another of said openings permits passage of more than one slide, wherein said another of said openings comprises means for ejecting slides which have stuck together.

15. The apparatus of claim 13, wherein the depositing means comprises a platform which is distinct from the carriage, wherein slides having blood smears are lifted onto the platform.

16. The apparatus of claim 15, further comprising ramp means for lifting slides from the carriage onto the platform.

* * * * *